(12) United States Patent
Kang et al.

(10) Patent No.: US 8,308,913 B2
(45) Date of Patent: Nov. 13, 2012

(54) APPARATUS FOR RECOVERING ACRYLIC ACID

(75) Inventors: Seong Pil Kang, Daejeon (KR); Seok Kwan Choi, Daejeon (KR); Kyoung Su Ha, Daejeon (KR); Jun Seok Ko, Seoul (KR); Boo Gon Woo, Daejeon (KR); Young Bae Kim, Jeollanam-do (KR)

(73) Assignee: LG Chem, Ltd., Seoul (KR)

( * ) Notice: Subject to any disclaimer, the term of this patent is extended or adjusted under 35 U.S.C. 154(b) by 148 days.

(21) Appl. No.: 12/565,359

(22) Filed: Sep. 23, 2009

(65) Prior Publication Data

US 2010/0012476 A1  Jan. 21, 2010

Related U.S. Application Data

(62) Division of application No. 11/116,367, filed on Apr. 28, 2005, now Pat. No. 7,612,231.

(30) Foreign Application Priority Data

Apr. 29, 2004  (KR) ......................... 10-2004-0029872

(51) Int. Cl.
 *B01D 1/22* (2006.01)
 *B01D 3/10* (2006.01)
 *B01D 3/28* (2006.01)
 *C07C 51/44* (2006.01)

(52) U.S. Cl. ..... 202/154; 159/5; 159/901; 159/DIG. 16; 202/158; 202/172; 202/188; 202/205; 422/187; 562/600

(58) Field of Classification Search ............... 159/5, 49, 159/901, DIG. 16; 202/154, 158, 172, 188, 202/205; 203/72, 73, 78, 80, 98, DIG. 21; 422/187; 562/600

See application file for complete search history.

(56) References Cited

U.S. PATENT DOCUMENTS

| 3,761,568 | A | * | 9/1973 | Brink et al. ................... 423/207 |
| 4,317,926 | A | | 3/1982 | Sato et al. |
| 4,408,125 | A | * | 10/1983 | Meuzelaar ..................... 250/288 |
| 5,471,937 | A | * | 12/1995 | Kosky et al. ................... 110/345 |
| 5,734,075 | A | | 3/1998 | Fauconet et al. |
| 5,910,603 | A | | 6/1999 | Aichinger et al. |

(Continued)

FOREIGN PATENT DOCUMENTS

EP  1382592 A  1/2004

(Continued)

OTHER PUBLICATIONS

English language abstract for Taiwanese Patent Publication No. 381078 B.

*Primary Examiner* — Virginia Manoharan
(74) *Attorney, Agent, or Firm* — Birch, Stewart, Kolasch & Birch, LLP

(57) ABSTRACT

Disclosed is an apparatus for recovering an acrylic acid from a mixture containing acrylic acid, acrylic acid dimer and impurities with high boiling point, including: an acrylic acid recovering device that comprises an acrylic acid distillation unit being present within an acrylic acid dimer pyrolysis tank, and is operated under reduced pressure; a separation column for removing impurities with high boiling point from the mixture which is introduced into the acrylic acid recovering device; and a line for introducing the mixture into the acrylic acid recovering device.

10 Claims, 2 Drawing Sheets

U.S. PATENT DOCUMENTS

| | | |
|---|---|---|
| 6,252,110 B1 | 6/2001 | Uemura et al. |
| 6,254,735 B1 * | 7/2001 | Watzenberger ............... 203/26 |
| 6,642,414 B2 | 11/2003 | Mitsumoto et al. |
| 2004/0220426 A1 | 11/2004 | Yada et al. |
| 2004/0220427 A1 | 11/2004 | Yada et al. |
| 2004/0267045 A1 | 12/2004 | Yada et al. |

FOREIGN PATENT DOCUMENTS

| | | |
|---|---|---|
| JP | 8-183756 A | 7/1996 |
| JP | 11-012222 A | 1/1999 |
| WO | WO-03/045889 A1 | 5/2003 |
| WO | WO-03/045892 A | 6/2003 |
| WO | WO-03/048100 A1 | 6/2003 |

* cited by examiner

APPARATUS FOR RECOVERING ACRYLIC ACID

This application is a Divisional of application Ser. No. 11/116,367 filed on Apr. 28, 2005 which has matured into U.S. Pat. No. 7,612,231, and for which priority is claimed under 35 U.S.C. §120. This application claims priority to application Ser. No. 10-2004-0029872 filed in Korea on Apr. 29, 2004 under U.S.C. §119, the entire contents of which are hereby incorporated by reference.

TECHNICAL FIELD

The present invention relates to a method for recovering acrylic acid and apparatus therefor. More particularly, the present invention relates to a method for recovering acrylic acid from a mixture containing acrylic acid, acrylic acid dimer and impurities with high boiling point, in a stable and efficient manner as well as apparatus therefor.

BACKGROUND ART

The method and apparatus according to the present invention can be applied after carrying out a process wherein acrylic acid-containing gas obtained from the vapor phase oxidation of propylene and/or acrolein in the presence of a catalyst is contacted with an absorbing solvent to collect acrylic acid in a solution state, the solution is rectified to recover crude acrylic acid, and the crude acrylic acid is purified in a separation tower to remove impurities with high boiling point.

In general, because the crude acrylic acid obtained by the above-described oxidation method contains impurities with high boiling point such as acrylic acid dimer and maleic acid, it is not economically advisable to discard such impurities as waste liquid due to the loss of acrylic acid. Acrylic acid has high polymerizability and polymerization of acrylic acid may occur during the above process. However, in addition to such polymerization, oligomerization such as dimerization and trimerization of acrylic acid may occur with ease. It is thought that such oligomerization results from serial reactions. During the above purifying process based on distillation, acrylic acid dimer is produced chiefly.

Production of acrylic acid dimer depends on temperatures and retention time. Additionally, it is not possible to inhibit production of acrylic acid dimer completely by adding a polymerization inhibitor. In conventional distillation processes, it is not evitable that acrylic acid dimer is produced in an amount of 1-5 wt %. Even if the impurities with high boiling point is removed by distillation, 5-50 wt % of acrylic acid dimer may be concentrated at the bottom of the distillation column. Therefore, it is not cost-efficient to discard the bottom liquid containing a high concentration of acrylic acid dimer without any post-treatment.

To solve the above problems, methods for recovering acrylic acid by pyrolysis of acrylic acid dimer into acrylic acid are suggested in Japanese Patent Publication Nos. 1970-19281B2, 1976-91208A, 1986-36501B2, 1999-12222A, etc.

The method disclosed in Japanese Patent Publication No. 1999-12222A uses an acrylic acid recovering column having a distillation tower and thin film evaporator, separated from a dimer pyrolysis unit. However, the method has a problem in that polymerization of acrylic acid may occur at a duct connecting the recovering column with the pyrolysis unit. Additionally, it is not cost-efficient that at least two equipments should be added for the acrylic acid recovering column and the pyrolysis unit.

Further, according to the above method, the thin film evaporator is operated at reduced pressure and the pyrolysis unit is operated at atmospheric pressure. In this regard, the method uses a condenser in order to remove odors emitted from vapors generated by acrylic acid, acrylic acid dimer and various kinds of impurities with high boiling point. Therefore, when the system is operated for a long time, polymerization of acrylic acid may occur at the part of the condenser to cause troubles in operation, resulting in emission of bad odors toward the surroundings.

DISCLOSURE OF THE INVENTION

Therefore, the present invention has been made in view of the above-mentioned problems. It is an object of the present invention to provide a method and apparatus or recovering acrylic acid by pyrolysis of acrylic acid dimer into acrylic acid. Particularly, the present invention provides an economical method and apparatus for recovering acrylic acid, which simplify a conventional multi-step process carried out under reduced pressure alternately with atmospheric pressure, and improve the ratio of dimer decomposition and recovering yield of acrylic acid.

We have found that it is possible to recover acrylic acid efficiently and economically by using a novel apparatus comprising an acrylic acid distillation unit integrated with an acrylic acid dimer decomposition unit, wherein the apparatus is operated under reduced pressure. The present invention is based on this finding.

According to an aspect of the present invention, there is provided a method for recovering acrylic acid from a mixture containing acrylic acid, acrylic acid dimer and impurities with high boiling point, which comprises the steps of: introducing the mixture into an acrylic acid recovering device comprising an acrylic distillation unit integrated with an acrylic acid dimer pyrolysis tank; carrying out decomposition of acrylic acid dimer under reduced pressure at the lower part of the acrylic acid recovering device, while recovering acrylic acid by distillation from the top of the acrylic acid recovering device; and optionally recycling a portion of the solution obtained from the bottom of the acrylic acid recovering device to the upper part of the device.

According to another aspect of the present invention, there is provided an apparatus for recovering acrylic acid from a mixture containing acrylic acid, acrylic acid dimer and impurities with high boiling point, which comprises: an acrylic acid recovering device that comprises an acrylic acid distillation unit integrated with an acrylic acid dimer pyrolysis tank and is operated under reduced pressure; a line for introducing the mixture into the acrylic acid recovering device; and optionally, a line for recycling a portion of the solution obtained from the bottom of the acrylic acid recovering device to the upper part of the device, wherein decomposition of acrylic acid dimer is carried out under reduced pressure at the lower part of the acrylic acid recovering device, while acrylic acid is recovered by distillation from the top of the acrylic acid recovering device.

Hereinafter, the present invention will be explained in more detail.

The method according to the present invention can be applied after carrying out a process wherein acrylic acid-containing gas obtained from the vapor phase oxidation of propylene and/or acrolein in the presence of a catalyst is contacted with an absorbing solvent to collect acrylic acid in a solution state, the solution is rectified to recover crude acrylic acid, and the crude acrylic acid is purified in a separation tower to remove impurities with high boiling point.

Specifically, according to the present invention, acrylic acid-containing gas obtained from the vapor phase oxidation of propylene and/or acrolein in the presence of a catalyst is contacted with water to collect acrylic acid as aqueous solution, and the aqueous solution is distilled with an azeotropic solvent to recover crude acrylic acid. Next, the crude acrylic acid is purified at a column for separating out impurities with high boiling point. Then, acrylic acid can be recovered from the mixture obtained from the bottom liquid of the separation column with high efficiency.

FIG. 1 is a schematic view showing a preferred embodiment of the method according to the present invention.

The method according to the present invention essentially comprises the following steps:

(1) A mixture containing acrylic acid, acrylic acid dimer and impurities with high boiling point (for example, a mixture obtained from the bottom of separation tower A for separating impurities with high boiling point) is introduced into acrylic acid recovering device B comprising an acrylic acid distillation unit integrated with a pyrolysis tank according to the present invention.

Particularly, the integrated acrylic acid recovering device is set under such conditions of temperature and pressure that acrylic acid having a relatively low boiling point can be vaporized and acrylic acid dimer can be decomposed into acrylic acid monomer.

The present invention is characterized in that acrylic acid is vaporized and acrylic acid dimer is pyrolyzed under reduced pressure, for example a pressure of between 5 and 160 mmHg, preferably of between 10 and 150 mmHg. Particularly, vaporization of acrylic acid and pyrolysis of acrylic acid dimer are accomplished under substantially the same pressure. With regard to the expression of "substantially the same pressure", it means that the pressure is same excluding a pressure difference generated by a gravitational difference resulting from the height in the acrylic acid recovering device according to the present invention.

(2) The acrylic acid contained in the stream from the bottom of the distillation column and the acrylic acid obtained by pyrolysis of acrylic acid dimer as described hereinafter are vaporized and then recovered from the top of the acrylic acid recovering device.

The acrylic acid obtained from the top of the acrylic acid recovering device contains a significantly reduced amount of impurities such as acrylic acid dimer and maleic acid. Preferably, it contains 0-2 wt % of maleic acid and 0-0.1 wt % of acrylic acid dimer.

Kind of built-in distillation unit in the acrylic acid recovering device according to the present invention is not particularly limited. However, it is preferable to use a thin film evaporator for the purpose of more efficient operation, because such thin film evaporators cause high-viscosity acrylic acid to be coated on the wall surface thereof, thereby carrying out vaporization of acrylic acid sufficiently at the wall surface heated to 60-150° C.

Meanwhile, acrylic acid recovered from the acrylic acid recovering device may be recycled to the preceding purification unit.

(3) Materials having a relatively high boiling point, such as acrylic acid dimer, flow down along the wall surface of the acrylic acid recovering device toward the pyrolysis tank disposed at the downstream of the acrylic acid recovering device. Then, the materials are retained in the pyrolysis tank for a certain time to perform pyrolysis of acrylic acid dimer.

Preferably, the bottom temperature of the integrated acrylic acid recovering device according to the present invention, i.e., the bottom temperature of the lower pyrolysis tank ranges from 100° C. to 160° C., more preferably from 130° C. to 135° C., considering a pressure difference between the top and the bottom under reduced pressure. If the bottom temperature is too high, precipitation caused by maleic acid may be generated, resulting in a troublesome occlusion in terms of long-term operation.

Although the retention time at the bottom of the acrylic acid recovering device varies depending on the temperature where pyrolysis of acrylic acid dimer is performed, it is generally known that a retention time of between 20 and 50 hours is desirable. However, according to the present invention, it was found that pyrolysis under reduced pressure conditions needs a shorter retention time. It is possible to perform pyrolysis of acrylic acid dimer in a time of between 10 and 30 hours, which is shorter than the above-mentioned conventional retention time. It is generally known that pyrolysis carried out in a relatively short time may result in undesired decomposition, polymerization, etc. However, because pyrolysis is performed under reduced pressure according to the present invention, contrary to conventional pyrolysis performed under atmospheric pressure, pyrolyzed acrylic acid is easily vaporized under reduced pressure at a sufficiently high temperature at the bottom of the acrylic acid recovering device, resulting in being recovered at the top of the acrylic acid recovering device.

(4) Meanwhile, waste liquid is discharged from the bottom of the acrylic acid recovering device. The waste liquid comprises impurities containing a significantly reduced amount of acrylic acid dimer due to the above pyrolysis step.

Optionally, the waste liquid obtained from the bottom of the acrylic acid recovering device may be recycled to the top of the device and the remaining liquid may be discarded.

In the pyrolysis tank disposed at the lower part of the acrylic acid recovering device according to the present invention, acrylic acid dimer is pyrolyzed, thereby forming acrylic acid. However, it is preferable that at least a part of the waste liquid is recycled to the evaporator disposed at the upper part of the device in order to recover acrylic acid with an increased yield and to control the retention time. In order to recover acrylic acid more efficiently from the bottom liquid of the acrylic acid recovering device, recycle ratio to the thin film evaporator disposed at the upper part may be increased. However, it is preferable that the recycled ratio is 200-800 wt % based on the weight of the mixture containing acrylic acid, acrylic acid dimer and impurities with high boiling point, wherein the mixture is obtained from the bottom of the separation tower for removing impurities with high boiling point and then is supplied to the acrylic acid recovering device.

(5) In order to reduce concentration of acrylic acid dimer and impurities with high boiling point contained in the stream recovered from the top of the acrylic acid recovering device (B) and then recycled to the separation tower, the present invention can add a tray distillation column C whose theoretical plate number is 1-5 to the top of the acrylic acid recovering device, as shown in FIG. 2. By doing so, it is possible to increase the purity of acrylic acid at the top of the recovering device, and thus to ensure the operational stability of the separation column for removing impurities with high boiling point, to which the above-recovered acrylic acid is recycled.

The mixture to be introduced to the acrylic acid recovering device according to the present invention, which contains acrylic acid, acrylic acid dimer and impurities with high boiling point, comprises at least 10 wt % of acrylic acid dimer. Preferably, the present invention may be applied to a mixture containing 5-10 wt % of maleic acid in addition to acrylic acid, i.e., an acrylic acid-containing mixture purified through azeotropic distillation. For example, a mixture containing 25-70 wt % of acrylic acid, 30-70 wt % of acrylic acid dimer, 5-20 wt % of a polymerization inhibitor (hydroquinone, phenothiazine, copper dibutyldithiocarbamate, etc.) and other impurities with high boiling point can be treated according to the present invention.

BEST MODE FOR CARRYING OUT THE INVENTION

Reference will now be made in detail to the preferred embodiments of the present invention. It is to be understood that the present invention is not limited to the following Examples.

EXAMPLE 1

Acrylic acid-containing gas obtained by partial oxidation of propylene was subjected to a processing comprising an absorption, azeotropic separation and purification steps to provide the mixture containing acrylic acid, acrylic acid dimmer and impurities with high boiling point. The acrylic acid-containing mixture was introduced to an acrylic acid recovering device equipped with a thin film evaporator having an electric heating area of 3.5 m² at a flow rate of 250 kg per hour. The wall surface of the acrylic acid recovering device was maintained at a temperature of 150° C. and operated under a pressure of 75 mmHg. Acrylic acid was recovered from the top of the device at a rate of 175 kg per hour. The pyrolysis tank disposed at the lower part of the device was operated at a temperature of 135° C. and pyrolysis was performed in a retention time of 18 hours. Additionally, the bottom liquid was recycled to the top of the device at a flow rate of 870 kg per hour. The recycled liquid is about 350 wt % based on the weight of the acrylic acid-containing mixture that contains acrylic acid dimer, introduced to the acrylic acid recovering device. The remaining liquid was discarded to treat as waste oil. The composition of acrylic acid, acrylic acid dimer and other impurities with high boiling point in each stream is as follows.

|  | Acrylic acid | Acrylic acid dimer | Other impurities with high boiling point |
|---|---|---|---|
| Stream introduced into device | 51.81 | 15.57 | 32.62 |
| Stream recovered from top of device | 83.95 | 1.03 | 15.02 |
| Waste liquid | 4.7 | 25.3 | 70.0 |

(expressed in wt %)

After operation for 4 months under the above conditions, the device could be operated in a stable manner without a significant change in concentration of acrylic acid or acrylic acid dimmer in the waste liquid. Further, there was no trouble caused by polymerization or the like.

EXAMPLE 2

Figure 1:
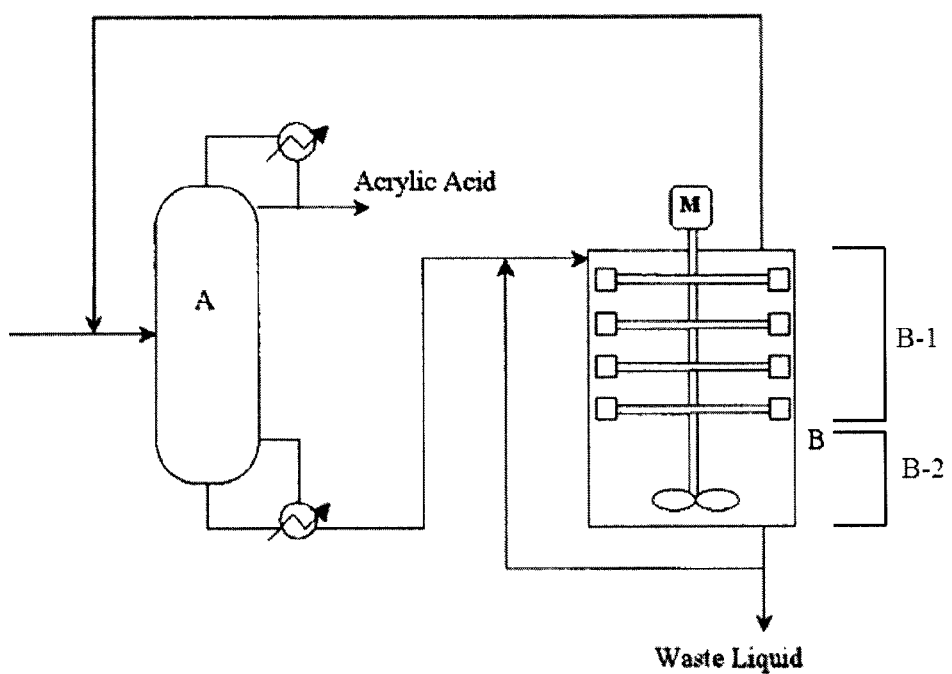
FIGS. 1 and 2 are schematic views each showing a preferred embodiment of the present invention, wherein reference letter A is a separation column for removing impurities with high boiling point, B is an acrylic acid recovering device comprising a thin film evaporator B-1 integrated with a pyrolysis tank B-2, C is a tray distillation column, and M is a motor.
Figure 2:
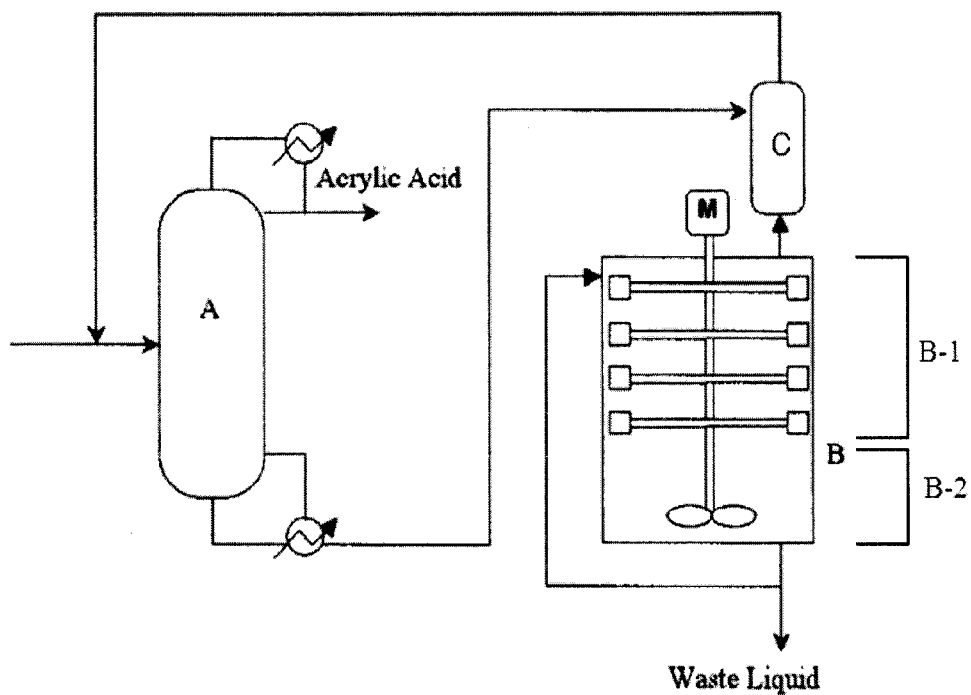

Example 1 was repeated, except that a tray distillation column whose theoretical plate number is 5 was added to the top of the recovering device as shown in FIG. 2 and that acrylic acid-containing mixture was introduced to the distillation column, in order to reduce the concentration of acrylic acid dimer and impurities with high boiling point in the stream recovered from the top of the acrylic acid recovering device according to the present invention and then recycled to the preceding purification stage for removing impurities with high boiling point. The wall temperature of the thin film evaporator was controlled so that the bottom temperature of the distillation column is 90° C., and the distillation column was operated at a reflux ratio of 0.7. As a result, the composition of the stream recycled to the preceding separation column was 99.8 wt % of acrylic acid, 0.06 wt % of dimer and the balance amount of impurities.

Industrial Applicability

As can be seen from the foregoing, according to the method of the present invention, decomposition of acrylic acid dimer is carried out efficiently by using an integrated system of distillation unit and pyrolysis tank, which can be operated under reduced pressure simultaneously. Therefore, it is possible to reduce the concentration of acrylic acid discharged as waste liquid and to increase the yield of acrylic acid, while maintaining the temperature of the pyrolysis tank at a reduced temperature, so that the method can be cost-efficient. In brief, according to the present invention, it is possible to recover acrylic acid efficiently by carrying out pyrolysis of acrylic acid dimer. Additionally, it is possible to operate the apparatus for carrying out the method for a long time in a stable manner.

While this invention has been described in connection with what is presently considered to be the most practical and preferred embodiment, it is to be understood that the invention is not limited to the disclosed embodiment and the drawings. On the contrary, it is intended to cover various modifications and variations within the spirit and scope of the appended claims.

The invention claimed is:

1. An apparatus for recovering an acrylic acid from a mixture containing acrylic acid, acrylic acid dimer and impurities with high boiling point, which comprises:
    a separation column for removing the impurities with high boiling point from the mixture;
    an acrylic acid recovering device that comprises a thin film evaporator disposed at an upper part of the acrylic acid device and being integrated with an acrylic acid dimer pyrolysis tank disposed at a lower part of the acrylic device, wherein the thin film evaporator and the acrylic acid dimer pyrolysis tank are configured to operate at the same pressure under reduced pressure;
    a line for introducing the mixture into the acrylic acid recovering device; and
    a line for recovering the acrylic acid by distillation from the top of the acrylic acid recovering device,
    wherein the pyrolysis of the acrylic acid dimer and the vaporization of the acrylic acid are carried out in the acrylic acid recovering device.

2. The apparatus according to claim 1, which further comprises a line for recycling a portion of a solution obtained from the bottom of the acrylic acid recovering device to the acrylic acid recovering device.

3. The apparatus according to claim 1, which further comprises a line for recycling a stream recovered from the top of the acrylic acid recovering device to the separation column.

4. The apparatus according to claim 1, which further comprises a tray distillation column having a theoretical plate number of 1-5 being placed onto the top of the acrylic acid recovering device.

5. The apparatus according to claim 4, wherein the tray distillation column is located between the top of the acrylic acid recovering device and the separation column.

6. An apparatus for recovering an acrylic acid from a mixture containing acrylic acid, acrylic acid dimer and impurities with high boiling point, which comprises:

a separation column for removing the impurities with high boiling point from the mixture;

an acrylic acid recovering device consisting essentially of a thin film evaporator disposed at an upper part of the acrylic acid device and being integrated with an acrylic acid dimer pyrolysis tank disposed at a lower part of the acrylic device, wherein the thin film evaporator and the acrylic acid dimer pyrolysis tank are configured to operate at the same pressure under reduced pressure;

a line for introducing the mixture into the acrylic acid recovering device; and a line for recovering the acrylic acid by distillation from the top of the acrylic acid recovering device, wherein the pyrolysis of the acrylic acid dimer and the vaporization of the acrylic acid are carried out in the acrylic acid recovering device.

7. The apparatus according to claim 6, which further comprises a line for recycling a portion of a solution obtained from the bottom of the acrylic acid recovering device to the acrylic acid recovering device.

8. The apparatus according to claim 6, which further comprises a line for recycling a stream recovered from the top of the acrylic acid recovering device to the separation column.

9. The apparatus according to claim 6, which further comprises a tray distillation column having a theoretical plate number of 1-5 being placed onto the top of the acrylic acid recovering device.

10. The apparatus according to claim 9, wherein the tray distillation column is located between the top of the acrylic acid recovering device and the separation column.

\* \* \* \* \*